United States Patent [19]

Drake

[11] Patent Number: 4,550,097
[45] Date of Patent: Oct. 29, 1985

[54] CATALYST FOR THE PRODUCTION OF ALLYL ACETATE

[75] Inventor: Charles A. Drake, Nowata, Okla.

[73] Assignee: Phillips Petroleum Company, Bartlesville, Okla.

[21] Appl. No.: 642,464

[22] Filed: Aug. 20, 1984

[51] Int. Cl.$^4$ .................. B01J 21/08; B01J 23/78; B01J 23/84
[52] U.S. Cl. .................. 502/170; 502/243; 502/328; 560/243; 560/245
[58] Field of Search .................. 502/170, 243, 328; 560/243, 245

[56] References Cited

U.S. PATENT DOCUMENTS

| | | | |
|---|---|---|---|
| 3,221,045 | 11/1965 | McKeon et al. | 260/497 |
| 3,274,238 | 9/1966 | Kojer et al. | 260/497 |
| 3,600,429 | 8/1971 | Kronig et al. | 260/475 N |
| 3,925,452 | 12/1975 | Swedenk et al. | 260/497 A |
| 3,939,199 | 2/1976 | Fernholz et al. | 260/469 |
| 3,950,400 | 4/1976 | Fernholz et al. | 260/497 A |
| 3,960,930 | 6/1976 | Clark | 260/475 N |
| 3,965,152 | 6/1976 | Smith et al. | 260/491 |
| 3,965,153 | 6/1976 | Smith et al. | 260/491 |
| 3,965,154 | 6/1976 | Smith et al. | 260/491 |
| 4,010,198 | 3/1977 | Roscher et al. | 260/497 A |
| 4,056,563 | 11/1977 | Boyadzhian et al. | 560/245 |
| 4,133,962 | 1/1979 | Fernholz et al. | 560/245 |
| 4,158,737 | 6/1979 | Bartach | 560/245 |
| 4,409,396 | 10/1983 | Dempf et al. | 560/245 |

FOREIGN PATENT DOCUMENTS 1101055  1/1968  United Kingdom .............. 560/243

*Primary Examiner*—W. J. Shine
*Attorney, Agent, or Firm*—Howard D. Doescher

[57] ABSTRACT

A process for providing high space time yields in the acetoxylation of propylene involving the use of a catalyst consisting essentially of palladium, potassium, bismuth, and a promoting amount of magnesium or a combination of magnesium and barium.

11 Claims, No Drawings

4,550,097

CATALYST FOR THE PRODUCTION OF ALLYL ACETATE

BACKGROUND

This invention relates to a process for the production of allyl acetate. More particularly the present invention relates to the production of allyl acetate by the acetoxylation of propylene.

It is known that allyl acetate can be produced by reacting propylene, oxygen, and acetic acid over a palladium-containing catalyst. Numerous examples of promoters for the catalyst are reported in the literature. One of the more effective types of catalysts are those comprising palladium, potassium, and bismuth supported on an inert support. Even with such catalysts the optimum conditions have been found to give only about 5–10% conversion of the propylene, with no more than about 90% selectivity to allyl acetate for a space time yield of about 250–320 grams of allyl acetate per liter of catalyst per hour.

Obviously, it would be desirable to have a process which provided still better selectivity, conversion, or space time yield.

An object of the present invention is to provide an improved process for the acetoxylation of propylene.

Still another object of the present invention is to provide a composition of matter suitable for use as a acetoxylation catalyst.

SUMMARY OF THE INVENTION

In accordance with the present invention a process is provided for preparing allyl acetate comprising reacting propylene, acetic acid, and oxygen under suitable reaction conditions in the presence of a catalyst consisting essentially of palladium, potassium, bismuth, and a promoting amount of magnesium and optionally barium, deposited on a support.

DETAILED DESCRIPTION

The catalysts of the present invention are prepared by depositing the active components on the support and subsequently drying the resulting composite.

The supports include those typically used for acetoxylation catalysts. Examples include silica, aluminum oxide, aluminum silicates, silicates, titanium oxide, zirconium oxide, titanates, pumice silicium carbide, silica gel, spinels, and mixtures thereof. It is preferred to use supports having a high chemical resistance to water and acetic acid such as silica for example. Especially suitable are silica having a nitrogen surface area in the range of 40 to 350 m$^2$/g.

The palladium of the catalyst can be in the form of free palladium metal or in the form of a compound of palladium which is preferably free of halogens, sulfur, and nitrogen. Examples of such compounds include palladium acetate, palladium propionate, palladium acetylacetonate or palladium hydroxide. It is currently preferred to employ a palladium carboxylate, especially palladium acetate.

The other active components are applied in the form of acetates or compounds which will be converted to acetate either during the catalyst prep or during the acetoxylation process. Examples include the formates, propionates, hydroxides, carbonates, phosphates, borates, citrates, tartrates, or lactates of the other active metal components.

The catalyst can be prepared in many different ways, for example a compound of the metal can be dissolved in a solvent, the support impregnated with the resulting solution and then dried. It is also possible, however, to impregnate the support successively with the components which can then be converted, if required, by an intermediate treatment, such as calcination, or chemical reactions such as for example treatment with solutions of an alkali metal hydroxide, alkali metal carbonate or a reducing agent. The catalysts can be prepared from a compound containing sulfur, nitrogen or halogen, which compound is then converted on the support into an insoluble compound which is substantially free of sulfur, nitrogen or halogen.

The currently preferred technique of preparing the catalyst, however, involves dissolving the metal components in glacial acetic acid, then impregnating the support, and then drying the resulting solid.

The amount of palladium employed on the catalyst can vary from about 1 to about 3 weight percent, most preferably about 1 to about 2 weight percent based on the weight of the support.

The amount of potassium can vary from about 3 to about 7 weight percent, more preferably about 4 to about 5 weight percent based on the weight of the support.

The amount of bismuth can vary from about 1 to about 3 weight percent, more preferably about 1.5 to 2.5 weight percent based on the weight of the support.

The magnesium, and barium, when employed, should be present in an amount sufficient to result in an improved selectivity or space time yield over a catalyst containing only Pd, Bi, and K. The specific amount needed will vary somewhat depending upon the amounts of Pd, Bi and K in the catalyst. Typically, the amount of magnesium will be at least about 0.2 weight percent and less than 0.5 weight percent, most preferably about 0.3 weight percent based on the weight of the support. The amount of barium will typically be at least 1 weight percent and no greater than 2 weight percent, most preferably about 1 weight percent.

In carrying out the acetoxylation propylene, oxygen, and acetic acid in the gaseous phase are contacted with the inventive catalyst at a temperature in the range of about 100° C. to about 250° C. and pressures of 1 to 25 absolute atmospheres. It is advantageous to use a concentration ratio which ensures that the reaction mixture does not attain the known explosion limits. The simplest way to do this is to keep the concentration of oxygen low, e.g. about 3 to 8% of the total feed employed. Generally, the non-reacted products may be recycled in a cyclic process.

It has been typically noted that the preferred results are obtained if the reaction is carried out at a temperature in the range of about 160° C. to about 180° C. and a pressure of about 42 to 120 psig, more preferably 75 to 100 psig.

The reaction mixture may also contain diluent gas which does not adversely affect the reaction such as nitrogen, carbon dioxide, and saturated hydrocarbons.

It is also within the scope of the invention to include water along with the reactants supplied to the catalyst. In fact it has been found that in many cases the inclusion of certain amounts of water with the reactants can result in further improvements in the conversion and in some cases the selectivity as well. Accordingly, in order to obtain the best space time yield it is recommended that water be included with the reactants. The amount of water employed is generally in the range of about 10 to about 30 weight percent of the acetic acid, more preferably about 15 to 25 weight percent.

The rate of contact of reactants and catalyst can vary over a wide range depending upon the conditions employed. Typically, however, the acetic acid would be supplied at a rate of about 0.4 to about 1.2 volumes per volume of catalyst per hour, more preferably about 0.7 to 0.9. The propylene would typically be supplied at a rate sufficient to provide about 0.5 to about 2 grams of propylene per milliliter of catalyst per hour, more preferably about 0.7 to about 1.5 g/ml/hr.

A further understanding of the present invention and the advantages that it provides will be provided by the following examples.

In the following examples the general procedure involved in preparing the catalysts involved dissolving the metal salts in glacial acetic acid, immersing the support with the solution, soaking the support for 2 hours. Then the liquid was removed using a rotary evaporator and the catalyst dried by heating for 3 hours in a convection oven at 120° C. The support employed was a silica sold by Davison Chemical Co. as high surface area silica number G-59 of 8-12 mesh. The acetoxylations were carried out in a metal pipe ½" by 20" packed with 50 ml of catalyst. Heat was supplied via a steam jacked around the pipe. After oxidation was established it was continued for about 3 hours and then a total sample of the reactor effluent was taken for 2 hours. The products were analyzed on a 5880 Hewlett Packard gas chromatograph using a ⅛"×36" Poropak Q column. The quantities of oxidation products were used to calculate conversion, selectivity and catalyst productivity using the following formulas:

$$\text{propylene conversion} = \frac{\text{moles allyl acetate} + \tfrac{1}{3}\text{ moles CO}_2 \times 100\%}{\text{moles propylene}}$$

$$\text{allyl acetate selectivity} = \frac{\text{moles allyl acetate} \times 100\%}{\text{moles allyl acetate} + \tfrac{1}{3}\text{ moles CO}_2}$$

$$\text{catalyst productivity (STY)} = \frac{\text{wt allyl acetate}}{\text{liter of catalyst/hr}}$$

EXAMPLE I

A series of catalysts were prepared using the acetates of Pd, K, and Bi to evaluate the effect of varying the levels of those metals. The results of the employment of those catalysts are summarized in Table I.

TABLE I

EFFECT OF CATALYST COMPONENT CONCENTRATIONS ON REACTION RESULTS

| Run No.[1] | Propylene, g/l/hr | Pd,[2] % | K,[2] % | Bi,[2] % | Selectivity, % | Conversion, % | STY, g/l/hr |
|---|---|---|---|---|---|---|---|
| 1 | 75 | 1.2 | 4.8 | 2 | 85.4 | 7.0 | 213 |
| 2 | 75 | 1.5 | 4.8 | 2 | 90.3 | 7.8 | 250 |
| 3 | 75 | 2.25 | 4.8 | 2 | 88.0 | 9.5 | 300 |
| 4 | 75 | 1.5 | 3.2 | 2 | 82.7 | 9.6 | 283 |
| 5 | 75 | 1.5 | 4.8 | 2 | 90.3 | 7.8 | 250 |
| 6 | 75 | 1.5 | 6.4 | 2 | 88.4 | 5.3 | 167 |
| 7 | 75 | 1.5 | 4.8 | 1 | 69.0 | 8.5 | 210 |
| 8 | 75 | 1.5 | 4.8 | 2 | 90.3 | 7.8 | 250 |
| 9 | 75 | 1.5 | 4.8 | 3 | 61.1 | 6.9 | 151 |

FOOTNOTES:
[1] Reaction Conditions: 42 ml/hr acetic acid, 4.5 l/hr O₂, 75 psig pressure, 180° C.
[2] Weight percent based on the support The data of runs 1-3 shows that as the level of palladium rose, so did the propylene conversion and productivity. However, optimum selectivity appeared to occur at about 1.5 wt % Pd. The data of runs 4-6 shows that the conversion and STY declined as the amount of potassium was increased from 3 wt %. However, optimum selectivity was observed with 4.8 wt % potassium. Runs 7-8 employ varying levels of bismuth. The runs indicate that the best results are obtained with the amount of bismuth is in the range of 1 to 3 weight percent.

EXAMPLE II

Another series of catalysts were prepared using yet other metals of the type which have been suggested for use as promoters for Pd-based acetoxylation catalysts. The results obtained of those catalysts is summarized in Table II.

TABLE II

STUDY OF THE EFFECTS OF METAL ADDITION TO THE Pd—K—Bi OXIDATION CATALYST

| Run No.[1] | Pd,[2] % | KOAc,[2] % | Bi,[2] % | Other,[3] % | Selectivity % | Conversion, % | STY g/l/hr |
|---|---|---|---|---|---|---|---|
| 10 | 1.5 | 4.8 | 2 | — | 90.9 | 10.0 | 323 |
| 11 | 1.5 | 4.8 | 2 | 2% Cd | 65.4 | 7.2 | 168 |
| 12 | 1.5 | 4.8 | 2 | 0.4% RE[4] | 82.0 | 9.2 | 268 |
| 13 | 1.5 | 4.8 | 2 | 1.5% Sb | 64.0 | 8.9 | 203 |
| 14 | 1.5 | 4.8 | 2 | 2% Pb | 90.7 | 7.2 | 235 |
| 15 | 1.5 | 4.8 | 2 | 2% Mg | 92.6 | 7.2 | 239 |
| 16 | 1.5 | 4.8 | 2 | 2% Ca | 81.8 | 6.7 | 196 |
| 17 | 1.5 | 4.8 | 2 | 2% Ba | 83.7 | 7.4 | 220 |
| 18 | 1.5 | 4.8 | 2 | 2% Sr | 83.0 | 10.7 | 316 |
| 19 | 1.5 | 4.8 | 2 | 2% Cs | 85.1 | 11.8 | 360 |

FOOTNOTES:
[1] Reaction Conditions: 4.5 l/hr O₂, 42 ml/hr acetic acid, 180° C., propylene 75 g/hr
[2] Weight percent based on support
[3] Weight percent metal acetate added to support
[4] A mixture of rare earth metal acetates The run using magnesium stands out in that it alone gave better selectivity than the control catalyst of run 10.

EXAMPLE III

Still another series of catalysts were prepared employing magnesium as a catalyst additive. The results of the use of those catalysts is summarized in Table III. (Runs 10 and 7 are included in the Table for ease of comparison.)

TABLE III

EFFECT OF MAGNESIUM LEVELS ON BASIC Pd—K—Bi CATALYST

| Run No.[1] | Temp., C. | Propylene, g/hr | Pd,[2] % | K,[2] % | Bi,[2] % | Mg,[2] % | Selectivity, % | Conversion, % | STY, g/l/hr |
|---|---|---|---|---|---|---|---|---|---|
| 10 | 180 | 75 | 1.5 | 4.8 | 2 | — | 90.9 | 10.0 | 323 |
| 20 | 180 | 75 | 1.5 | 4.8 | — | .34 | 79.9 | 7.3 | 207 |

TABLE III-continued

EFFECT OF MAGNESIUM LEVELS ON BASIC Pd—K—Bi CATALYST

| Run No.[1] | Temp., C. | Propylene, g/hr | Pd,[2] % | K,[2] % | Bi,[2] % | Mg,[2] % | Selectivity, % | Conversion, % | STY, g/l/hr |
|---|---|---|---|---|---|---|---|---|---|
| 21 | 180 | 75 | 1.5 | 4.8 | 2 | .17 | 86.8 | 8.5 | 262 |
| 7 | 180 | 75 | 1.5 | 4.8 | 1 | — | 69.0 | 8.5 | 210 |
| 22 | 180 | 75 | 1.5 | 4.8 | 1 | .34 | 88.0 | 9.9 | 310 |
| 23 | 180 | 75 | 1.5 | 4.8 | 1 | .17 | 62.7 | 3.6 | 81 |
| 24 | 180 | 75 | 1.5 | 4.8 | 2 | .51 | 88.1 | 7.1 | 222 |
| 25 | 180 | 75 | 1.5 | 4.8 | 2 | .34 | 92.6 | 7.2 | 239 |
| 26 | 180 | 35 | 1.5 | 4.8 | 2 | .34 | 93.6 | 14.6 | 227 |
| 27 | 180 | 100 | 1.5 | 4.8 | 2 | .34 | 94.4 | 4.0 | 183 |
| 28 | 170 | 35 | 1.5 | 4.8 | 2 | .34 | 95.6 | 10.1 | 161 |

FOOTNOTES:
[1]Reaction Conditions: 42 ml/hr acetic acid, 4.5 l/hr $O_2$.
[2]Weight percent based on the support.

Run 20 involved the use of a catalyst containing Mg but not Bi. The conversion and selectivity were both inferior to comparable inventive catalysts. A comparison of runs 10, 21, 23, and 24 indicates that better results would be obtained if the Mg level was at least about 0.2 wt % and less than about 0.5 wt %. A comparison of runs 7, 22, and 23 also reveals that a Mg level of at least about 0.2 wt % would be preferred. The best results were obtained using a low propylene rate (35 g/hr) to give high conversion and a reduced temperature (170° C.) to improve selectivity.

EXAMPLE IV

Still another series of catalysts were prepared to determine if a material could be found which would promote even the Pd/K/Bi/Mg catalyst. A summary of the results is provided in Table IV.

TABLE IV

SUMMARY OF THE EFFECTS OF ADDITION OF Ba OR Ca TO THE Pd—K—Bi—Mg CATALYST

| Run No.[1] | Temp., C. | Propylene, g/hr | Pd,[2] % | KOAc,[2] % | Bi,[2] % | Promoter,[3] 1 | Promoter,[3] 2 | Selectivity, % | Conversion, % | STY, g/l/hr |
|---|---|---|---|---|---|---|---|---|---|---|
| 10 | 180 | 75 | 1.5 | 4.8 | 2 | — | — | 90.9 | 10.0 | 323 |
| 15 | 180 | 75 | 1.5 | 4.8 | 2 | 2% Mg | — | 92.6 | 7.2 | 239 |
| 29 | 180 | 75 | 1.5 | 4.8 | 2 | 2% Mg | 2% Ca | 78.4 | 5.2 | 140 |
| 30 | 180 | 75 | 1.5 | 4.8 | 2 | 2% Mg | 2% Ba | 93.6 | 10.3 | 343 |
| 31 | 180 | 75 | 1.5 | 4.8 | 2 | 2% Mg | 4% Ba | 87.3 | 5.7 | 178 |
| 32 | 180 | 75 | 1.5 | 4.8 | 2 | — | 2% Ba | 83.7 | 7.4 | 220 |

FOOTNOTES:
[1]Reaction Conditions: 42 ml/hr acetic acid, 4.5 l/hr $O_2$
[2]Weight percent based on support
[3]Weight percent metal acetate added to support Run 29 shows that calcium was ineffective in providing additional improvement. Run 30 shows that about 1.1 weight percent barium based on the support provided an improvement in both conversion and selectivity. Run 31 shows that if the amount of barium added is too great the improvement is not obtained. Run 32 shows that the barium used without magnesium is not as effective as magnesium used without the barium.

EXAMPLE V

Another series of runs were made to determine the effect that incorporating water in the feed would have on the inventive catalysts. The results are summarized in Table V.

TABLE V

EFFECT OF $H_2O$ ADDITION ON PROPYLENE OXIDATION

| Run No.[1] | Temp., C. | Press., psig | Propylene, g/hr | Pd,[2] % | K,[2] % | Bi,[2] % | Mg,[2] % | $H_2O$,[3] % | Selectivity, % | Conversion, % | STY, g/l/hr |
|---|---|---|---|---|---|---|---|---|---|---|---|
| 33 | 180 | 75 | 75 | 1.5 | 4.8 | — | — | — | 61.0 | 8.4 | 184 |
| 34 | 180 | 75 | 75 | 1.5 | 4.8 | — | — | 20 | 89.0 | 5.4 | 175 |
| 35 | 160 | 75 | 35 | 1.5 | 4.8 | 2 | .34 | — | 88.1 | 7.3 | 106 |
| 36 | 160 | 75 | 35 | 1.5 | 4.8 | 2 | .34 | 20 | 91.8 | 11.9 | 181 |
| 37 | 160 | 75 | 75 | 1.5 | 4.8 | 2 | .34 | 20 | 97.7 | 9.1 | 316 |
| 38 | 160 | 75 | 75 | 1.5 | 4.8 | 2 | .34 | 10 | 75.7 | 10.7 | 289 |
| 39 | 160 | 75 | 75 | 1.5 | 4.8 | 2 | .34 | 30 | 34.2 | 9.8 | 56 |

FOOTNOTES:
[1]Reaction Conditions: 42 ml/hr solvent, 4.5 l/hr $O_2$
[2]Weight percent based on support
[3]Weight percent $H_2O$ based on acetic acid Run 34 demonstrates that the addition of water to a Pd/K catalyst increases selectivity but lowers conversion so that the space time yield is actually lower when the water is employed. In contrast runs 36 and 37 show that when water is employed in the feed using the inventive catalyst both selectivity and conversion are improved. Runs 38 and 39 shows that there is an optimum level of water somewhere between 10 and 30 weight percent, based on the acetic acid.

What is claimed is:
1. A catalyst suitable for the acetoxylation of propylene consisting essentially of metals on a support said metals consisting essentially of potassium, bismuth, palladium, and a promoting amount of magnesium or a combination of magnesium and barium.

2. A catalyst according to claim 1 wherein the catalyst contains 1 to 3 weight percent palladium, 3 to 7 weight percent potassium, and 1 to 3 weight percent bismuth, said weight percentages being based on the support.

3. A catalyst according to claim 2 wherein the magnesium is at least about 0.2 weight percent and less than 0.5 weight percent based on the weight of the support.

4. A catalyst according to claim 3 wherein said catalyst consists essentially of palladium, potassium, bismuth, magnesium, and support.

5. A catalyst according to claim 4 wherein said support is silica.

6. A catalyst according to claim 5 wherein said catalyst contains about 1 to about 2 weight percent palladium, about 4 to about 5 weight percent potassium, about 1.5 to about 2.5 weight percent bismuth, and about 0.3 weight percent magnesium based on the weight of the support.

7. A catalyst according to claim 6 wherein said catalyst is prepared by dissolving acetates of the metal components in glacial acetic acid, then impregnating said silica support, and then drying the resulting solid catalyst.

8. A catalyst according to claim 2 wherein said catalyst also contains barium and the barium is at least 1 weight percent and no greater than 2 weight percent based on the support.

9. A catalyst according to claim 8 wherein said support is silica.

10. A catalyst according to claim 9 wherein said catalyst contains about 1 to about 2 weight percent palladium, about 4 to about 5 weight percent potassium, about 1.5 to about 2.5 weight percent bismuth, and about 0.3 weight percent magnesium based on the weight of the support.

11. A catalyst according to claim 10 where said catalyst is prepared by dissolving acetates of the metal component in glacial acetic acid, then impregnating said silica support, and then drying the resulting solid catalyst.

* * * * *